(12) United States Patent
Loeb et al.

(10) Patent No.: US 6,845,193 B2
(45) Date of Patent: Jan. 18, 2005

(54) LASER CHANNELING DEVICES

(75) Inventors: Marvin P. Loeb, Huntington Beach, CA (US); L. Dean Crawford, Irvine, CA (US)

(73) Assignee: Trimedyne, Inc., Irvine, CA (US)

( * ) Notice: Subject to any disclaimer, the term of this patent is extended or adjusted under 35 U.S.C. 154(b) by 157 days.

(21) Appl. No.: 10/152,951

(22) Filed: May 21, 2002

(65) Prior Publication Data

US 2003/0219202 A1 Nov. 27, 2003

(51) Int. Cl.[7] ............................. G02B 6/32; A61B 18/18
(52) U.S. Cl. ........................................... 385/33; 606/15
(58) Field of Search ..................... 606/14–17; 385/31, 385/33–35, 115–119, 902

(56) References Cited

U.S. PATENT DOCUMENTS

| 4,695,697 | A | * | 9/1987 | Kosa ..................... 219/121.83 |
| 5,207,673 | A | * | 5/1993 | Ebling et al. ................. 606/16 |
| 5,361,316 | A | * | 11/1994 | Tanaka et al. ................ 385/35 |
| 5,579,423 | A | * | 11/1996 | Tanaka et al. ................ 385/35 |
| 5,782,825 | A | * | 7/1998 | Anderson ..................... 606/15 |
| 5,951,541 | A | * | 9/1999 | Simpson et al. ................ 606/7 |
| 6,053,911 | A | * | 4/2000 | Ryan et al. ................... 606/33 |
| 6,522,827 | B1 | * | 2/2003 | Loeb et al. ................. 385/147 |

* cited by examiner

*Primary Examiner*—Akm Enayet Ullah
*Assistant Examiner*—Scott A Knauss
(74) *Attorney, Agent, or Firm*—Olson & Hierl, Ltd.

(57) ABSTRACT

An optical fiber device for ablating a channel through a plaque deposit or a clot in a blood vessel is described. Laser energy is transmitted through one or a bundle of optical fibers to a quartz or fused silica cylinder, whose distal end surface has been made into a desired shape and sandblasted or carbon coated or both. The cylinder is received with a pocket defined in a sheath which surrounds the optical fibers. Moreover, the cylinder includes a circumferential recess and the sheath includes a circumferential rib which engages into the recess for securing the lens in the pocket. In one embodiment, the cylinder has a cavity formed therein and the distal end of the optical fiber extends into the cavity. In a further embodiment, the device is adapted to be guided along a wire extending through the pocket and an aperture defined in the sheath and/or a channel defined in the cylinder.

34 Claims, 5 Drawing Sheets

LASER CHANNELING DEVICES

FIELD OF THE INVENTION

The invention relates to medical devices and, more particularly, to laser devices for forming channels in occluded blood vessels.

BACKGROUND OF THE INVENTION

When plaque deposits in blood vessels obstruct flow, the plaque blockage is commonly surgically bypassed by extracting a little used blood vessel from the patient and connecting it to a source of blood above the blockage and to the vessel below the blockage, thus creating a bypass for blood to flow around the obstruction. However, bypass surgery entails significant morbidity and mortality, as well as substantial cost. Alternatively, in a procedure called balloon angioplasty, a catheter with a balloon mounted on the distal end thereof can be guided into and expanded within the blockage, to compress and, perhaps, fracture the plaque, thus permitting blood flow through the vessel to resume at least partially. However, the blockage typically recurs after balloon angioplasty procedures in up to 40% of the patients within six months.

Alternatively, excimer laser energy, which is capable of vaporizing tissue with only minimal thermal effect, can be transmitted through fiber optic catheters, such as the catheter described in U.S. Pat. No. 4,732,448 to Goldenberg, and can be used to vaporize plaque deposits in blood vessels. However, many vessels are not treatable with excimer laser catheters, either being too large, too tortuous to traverse or too completely blocked to admit a guidewire over which the catheter may be advanced. In vessels which can be treated with excimer laser catheters, the blockage recurs in up to 40% of the patients within six months. Likewise, mechanical atherectomy devices, such as rotating burrs and cutting devices, have been employed in vessels blocked by plaque, but the clinical results of mechanical atherectomy devices have been no better than balloon or excimer laser angioplasty.

Plaque deposits in blood vessels can also be treated by using stents, i.e., tiny coils of stainless steel or other materials, which are deposited within a ballooned or layered plaque deposit to help keep the vessel open to blood flow. However, blockages in stents recur in up to about 15% to 25% of the cases within six months, due to the in-growth of tissue in the vessel opening. Effectively reopening a blocked stent is often difficult or impossible.

In the late 1980s, Argon and Nd:YAG laser energy was used to melt and vaporize plaque in blood vessels. The laser energy was transmitted through an optical fiber whose distal end was encased in a bulbous metal cap, usually made of stainless steel, and which was rapidly heated to 400° C. or more in a few seconds by the laser energy, as described in co-owned U.S. Pat. Nos. 4,646,737, 4,662,368 and 4,773,413, which are fully incorporated herein by reference.

These laser devices, commonly referred to as "Hotip"™ devices, were able to make relatively smooth channels through vessel plaque deposits. However, in substantially occluded blood vessels with little blood flow to cool the Hotip™ device, temperatures often reached 800° C. or higher. Even at a temperature of 400° C., thermal energy radiating sideward from the metal tip could damage the wall of the blood vessel underlying the plaque if the device was not kept rapidly moving back and forth in the vessel during the lasing procedure and, after switching off the laser, for 5 to 10 seconds, while the device cooled. If the Hotip™ device remained static in a blood vessel, severe damage would occur.

When properly used, the initial success rate of the Hotip™ device in peripheral (leg) vessels was 89% and, over a period of 30 months, was comparable to the results of peripheral artery bypass surgery. However, in the early 1990s, sales of these devices declined sharply, after the publication of several reports of injuries to blood vessels in humans, mainly due to lateral radiation of heat and damage to the arterial wall as the result of the operator's failure to keep the tip moving back and forth during and after the lasing procedure. Hotip™ devices and their associated lasers, which enjoyed sales of more than $30 million in each of 1989 and 1990, are no longer sold in any substantial amount for this purpose.

Another laser device which has been used to vaporize plaque deposits includes an optical fiber with a metal fitting attached to its distal end which in turn is connected to a second metal fitting holding a lens of sapphire or synthetic sapphire, such as described in U.S. Pat. Nos. 4,592,353 and 4,693,244 to Daikuzono. With these devices, however, heat has a tendency to develop at the junction of the optical fiber and the sapphire lens due to scattering of light energy at the junction. This, in turn, heats the metal fittings and causes lateral radiation of thermal energy. In addition, such devices are expensive to manufacture and costly to the hospital.

Because of the various disadvantages associated with the use of the above laser devices used to treat occluded blood vessels, it would be desirable to be able to melt and vaporize plaque deposits safely in blood vessels and in a minimally invasive manner with an alternative simple, reliable, inexpensive, non-metallic device, which would not thermally damage the vessel wall underlying the plaque deposit and avoid the risks and cost of bypass surgery and the high occlusion recurrence rates currently associated with the use of balloon and excimer laser angioplasty and mechanical atherectomy devices.

SUMMARY OF THE INVENTION

A laser device for forming a channel through an occlusion or plaque in a blood vessel is provided. The device comprises a fiber optic conduit which is adapted to be coupled to a source of laser energy, a hollow sheath which covers distal end of the fiber optic conduit and defines a pocket, and a fiber optic lens in the pocket and adapted to receive and direct the laser energy emitted from the fiber optic conduit through the lens onto the occlusion and to form a channel therethrough.

In one embodiment of the invention, the exterior surface of the lens is sandblasted and/or coated with carbon to absorb laser energy and generate thermal energy which vaporizes the occlusion upon contact. In another embodiment, the lens extends beyond the end of the sheath and includes a cylindrical body terminating in either a distal spherical end face or a distal oval end face which has been sandblasted and/or coated with carbon. In yet another embodiment, a circumferential band on the exterior surface of the lens is sandblasted and/or carbon coated.

The lens may also include a cavity defined in the body thereof with the distal end of the fiber optic conduit received in the cavity. The cavity in the body of the lens may be rounded or defined by two spaced-apart side walls and either a concave or convex base therebetween which acts either as a convergent or divergent lens respectively. The optical fiber may be centered between said side walls by a gasket or an epoxy ring.

The lens may also include an exterior surface having a circumferential recess defined therein and the sheath includes a distal circumferential rib adapted to engage in the recess for securing the lens in the pocket of the sheath. The lens can also include proximal and distal end portions where the thickness of the proximal end portion is less than the thickness of the distal end portion so that the sheath surrounding the lens is flush with the distal end portion of the lens.

In still another embodiment, the sheath includes an exterior wall having a pocket and an aperture defined therein. For guiding such a device through the blood vessel, a wire extends through the pocket defined in the sheath and through the aperture. The wire may also extend through a tube affixed within a channel defined in the sheath.

DETAILED DESCRIPTION OF THE PREFERRED EMBODIMENTS OF THE INVENTION

The invention disclosed herein is, of course, susceptible of embodiment in many different forms. Shown in the drawings and described hereinbelow in detail are preferred embodiments of the invention. It is to be understood, however, that the present disclosure is an exemplification of the principles of the invention and does not limit the invention to the illustrated embodiments.

For ease of description, the laser angioplasty channeling devices embodying the present invention are described hereinbelow in their usual generally horizontal use orientation and terms such as upper, lower, vertical, etc., will be used herein with reference to this usual position.

Moreover, the FIGURES omit details of the lasing device structure such as, for example, the laser source, introducer sheaths and guiding catheters used in angioplasty applications and the structure of the optical fiber and the lens, all of which are known in the art and will be recognized by those skilled in the art as such. The detailed descriptions of such elements are not necessary to an understanding of the invention. Accordingly, such elements are herein represented only to the degree necessary to aid an understanding of the features of the present invention.

Lasers which may be used with the devices described below in detail include excimer, argon, KTP, diode, Nd:YAG, Holmium:YAG and Erbium:YAG, among others. If an excimer laser is used, the optical fibers should have a high OH or hydroxyl content. If an argon, KTP, diode or Nd:YAG laser is used, the optical fibers can be of conventional quartz or fused silica. If a Holmium:YAG laser is employed, the optical fibers should have a low OH or hydroxyl content. If an Erbium:YAG laser is used, an ultra-low OH or hydroxyl content or a sapphire or synthetic sapphire optical fiber should be used. Preferably, a diode or Nd:YAG laser would be most desirable, due to their relatively low cost, small size and high reliability.

Figure 1A:
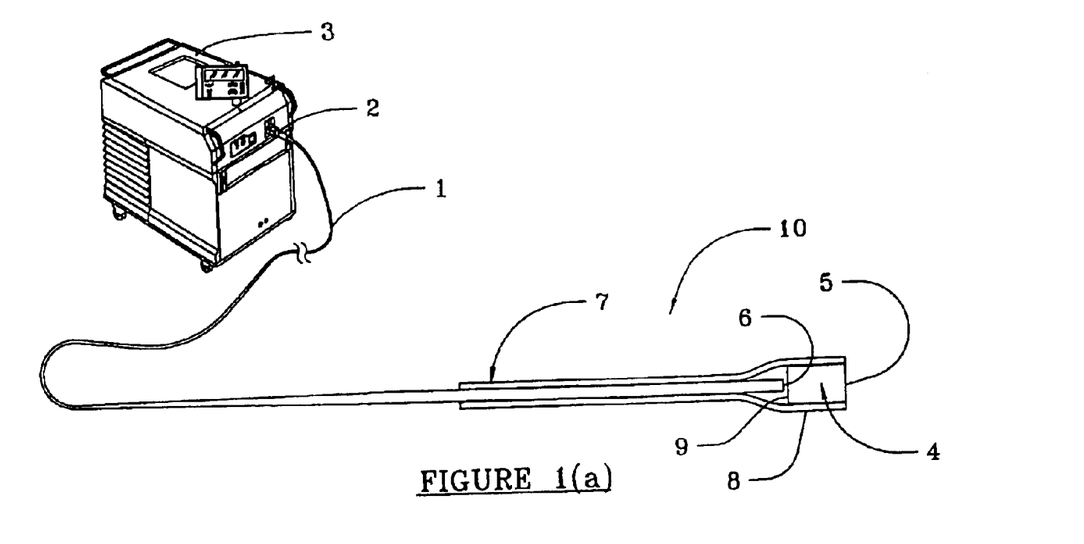
FIG. 1(a) is an enlarged, broken vertical cross-sectional view of a laser device according to the present invention, and a simplified perspective view of the laser source for the device.

FIG. 1(a) depicts a first angioplasty or channeling laser device 10 including a single optical fiber 1 which is optically coupled by a connector 2 to a source of laser energy 3, as known in the art. An elongate and tubular hollow sheath or cannula 7 extends and is heat shrunk over the distal end portion of the optical fiber 1 and terminates in a unitary generally cylindrically shaped distal end member which defines a pocket 8 adapted to receive a fiber optic lens 4 which, in the embodiment shown, is in the form of a cylinder. The sheath may be about 5 to 20 cm in length, but is preferably about 1 to 3 meters long to prevent accidental dislodgement of optical fiber 1. The fiber optic lens 4 includes a flat distal end face 5 and is positioned within the recess or pocket 8 in a relationship wherein the face 5 is positioned flush with the distal end face of the pocket 8. The proximal end face 9 of the cylinder 4 is positioned opposite and spaced from and parallel to the distal end face 6 of the optical fiber 1.

A single, flexible optical fiber 1 with a core diameter of about 365 to 660 microns can be used in relatively straight vessels, such as peripheral blood vessels, while a single optical fiber 1 with a core diameter of about 100 to 300 microns or a bundle of a multiplicity of very small, extremely flexible optical fibers, each with a core diameter of about 10 to 100 microns, can be used in small or tortuous vessels, such as the coronary arteries.

The devices of the present invention can also be employed to remove plaque blockages at bifurcations of blood vessels and in plaque blockages in vessels at the point where a coronary artery opens from the aorta (osteal openings), in which no "purchase" exists for a balloon catheter, laser catheter or mechanical atherectomy device. The devices of the present invention may also be used to vaporize tissue and plaque which has ingrown or formed inside a stent, and they may also be used to rapidly ablate a clot in a blood vessel.

Moreover, in accordance with the present invention, the fiber optic cylinder 4 comprises a short length of fused silica, quartz or synthetic sapphire optical fiber, about 2 to 12 mm in length, preferably about 4 to 8 mm in length, from which the buffer coat has been removed. Optical fiber 1 may be a single optical fiber or a bundle of optical fibers about 3 meters in length. The diameter of the cylinder 4 is preferably greater than the diameter of the optical fiber or bundle of optical fibers 1 to minimize the loss of laser energy and to minimize the heating which occurs at the junction of the optical fiber 1 and the cylinder 4 due to scattering of light.

The hollow sheath 7, is a thin tube of a heat shrinkable plastic material, such as Teflon® (PTFE) or Tefzel® (FEP) or the like, made by DuPont de Nemours of Wilmington, Del., which may be disposed either over the entire body of the optical fiber 1 and the cylinder 4 or, as shown in FIG. 1(a), only over the cylinder 4 and about the distal end portion of the optical fiber 1. In either case, the cylinder 4 is fixedly held in place, in apposition to the distal end face 6 of the optical fiber 1. The distal end face of cylinder 4 may be sandblasted and/or coated with carbon to absorb the laser energy, as aforesaid.

When a device as described in FIG. 1(a) was brought into contact with a clot of bovine blood in a glass tube with an inside diameter of 3 mm in a water bath at room temperature and 3 watts of Holmium:YAG laser energy (200 mj per pulse, 15 herty for 1 second at a wavelength of 2100) was transmitted through the device, a channel in the clot slightly larger than the outside diameter of the distal end of the device 10 was created as the device 10 was advanced therethrough.

FIGS. 1(b) through 12 depict various embodiments of the device 10. As such, elements of the devices shown in FIGS. 1(b) through 12 similar to the elements of the device 10 shown in FIG. 1(a) have been designated with the same first digit but different second and third digits corresponding to the particular figure being described.

Figure 1B:
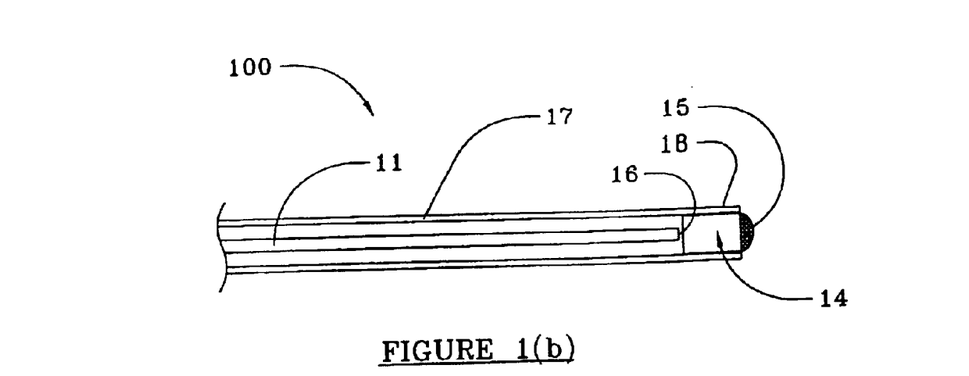
FIG. 1(b) is a partial enlarged, broken vertical cross-sectional view of another embodiment of the laser device of this invention before heat shrinking of a hollow sheath to the optical fiber.

FIG. 1(b) depicts a device embodiment 100 where the cylinder 14 is spaced from the distal end face 16 of the optical fiber 11 and the distal end face 15 of the cylinder 14 extends beyond the end of the cannula pocket member 18 and has been rounded and sandblasted and/or carbon coated so as to absorb the laser energy transmitted therethrough from the optical fiber 11. The cannula 17 is shown in its configuration before heat has been applied to shrink the cannula 17 against the fiber 11 as shown above in FIG. 1(a). The rounded distal end face 15 of the cylinder 14 can be coated with charcoal before assembly into the device 100, for example, by emitting laser energy through the cylinder 14 while its distal end face 15 is in contact with a combustible, cellulose material, such as wood or paper. When laser energy is transmitted through such a device 100, tissue in contact with the carbon coated distal end face 15 of the cylinder 14 is rapidly ablated. However, if the distal end face of cylinder 14 is not sandblasted and is only carbon coated, the carbon coating may not persist if the device 100 is used to melt or vaporize several centimeters of plaque in a long blockage, or several shorter lengths of plaque in one or more vessels.

Figure 4:
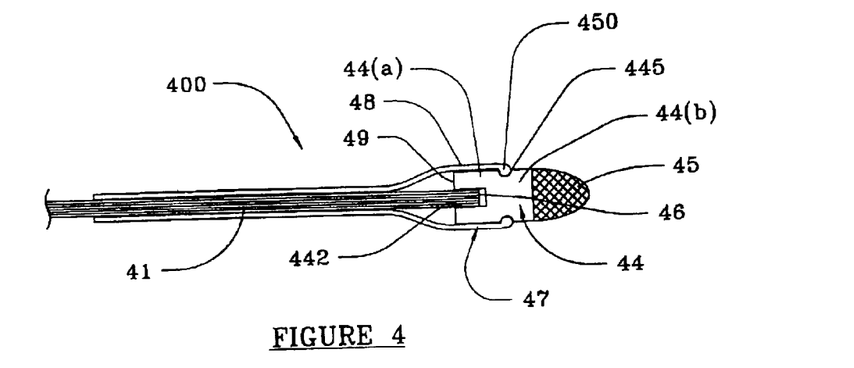
FIG. 4 is an enlarged, broken vertical cross-sectional view of another embodiment of a laser device similar to that of FIG. 1(b) including a bundle of optical fibers with distal ends disposed in a recess defined in the proximal end of a fiber optic lens.

It is well known that fused silica, quartz and sapphire are good conductors of light energy, but poor conductors of thermal energy. A glass, quartz or sapphire tipped laser angioplasty device 100 in accordance with the present invention and as shown in FIG. 1(b) where the distal end face of the cylinder 4 has been carbon coated or roughened by sand blasting, or both, can advantageously be used to rapidly melt or vaporize plaque when it comes into contact with the distal end face of the device 100. Infusion of a fluid, such as saline, over the distal end of the device as shown in FIG. 4 can reduce the temperature of the sidewall of the device, reducing the amount of thermal energy conducted or radiated sideward toward the vessel wall, while significantly reducing the time the operator must keep the device moving within the vessel while it cools.

When inserted into a plaque deposit and laser energy is transmitted through the device 100, plaque accumulates in the crevices, pits and imperfections in the sandblasted surface, which quickly chars and creates the same tissue effect as the above mentioned charcoal coating. However, the sandblasted surface is durable and can last through a significant number of uses. Of course, sandblasting followed by carbon coating can provide both the instant and long lasting benefits, respectively, of each.

In a test in room temperature air, 5 watts of continuous wave Nd:YAG laser energy (1064 nm wavelength) was transmitted for 2 seconds through a 550µ core diameter optical fiber, which had a 6 mm long, 2 mm core diameter fiber-optic cylinder 14 with a rough polished, flat distal end face 15 affixed to the distal end of the optical fiber, as described above. The temperature of the distal end face 15 of the cylinder 4 was 846° C. However, the temperature at the side of the cylinder 14 was only 49° C., less than the temperature at which tissue coagulation and damage occurs.

Figure 2:
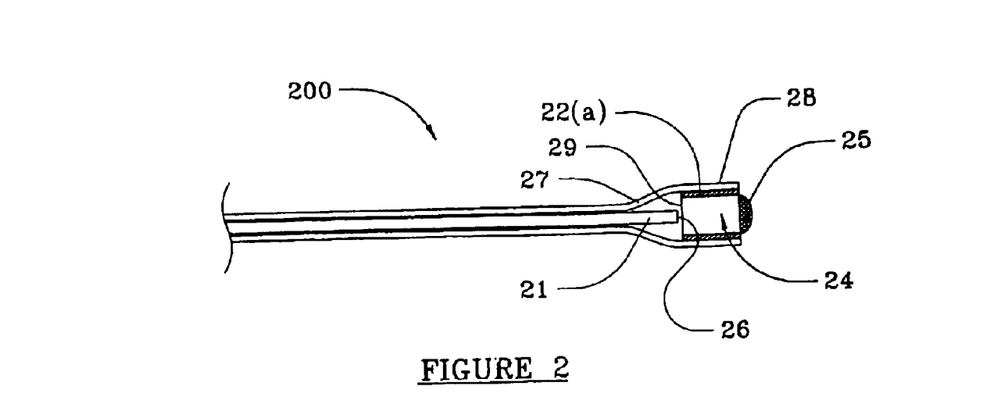
FIG. 2 is an enlarged, broken vertical cross-sectional view of the device, similar to that of FIG. 1(b), in which a ceramic sleeve is disposed at the distal end of the laser device between the heat shrunk hollow sheath and the exterior of the fiber optic lens.

FIG. 2 shows a device embodiment 200 where again the proximal end face 29 of the cylinder 24 is spaced from the distal end face 26 of the fiber 21, includes a rounded distal end face 25 similar to face 15 of device 100 and in which a ceramic sleeve 22(a) has been adhesively or friction fitted and surrounds the exterior peripheral surface of the cylinder 24. The heat shrunk sheath 27 extends over and surrounds the optical fiber 21 and the ceramic sleeve 22(a). The sleeve 22(a) prevents thermal damage to the cylindrically shaped distal end member 28 of the sheath 27 surrounding the cylinder 24 and further prevents the radiation of any heat laterally through the exterior peripheral surface of the cannula member 28.

Figure 3:
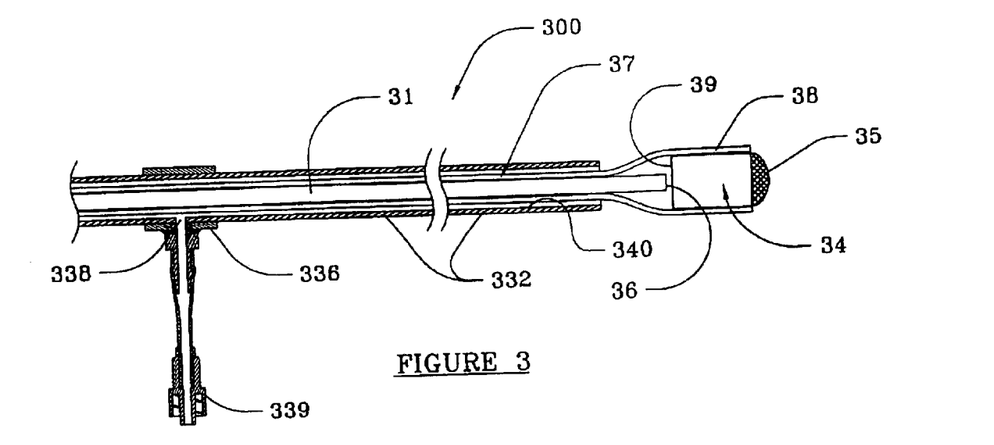
FIG. 3 is an enlarged, broken vertical cross-sectional view of the laser device of FIG. 2 positioned within the interior of an elongate outer catheter having a fluid infusion fitting associated therewith.

FIG. 3 depicts another device embodiment 300 which differs from the FIG. 1(a) device embodiment 10 in that the embodiment 300 includes an outer tubular catheter 332 which surrounds the heat shrunk sheath 37 and the fiber 31 and terminates at a point proximal to the distal cannula end member 38. The fiber 31, as in the earlier embodiments, includes a distal end face 36 which is spaced from the proximal end face 39 of the cylinder 34. The outer catheter 332 is spaced from the sheath 37 to create and define a fluid passageway 340 therebetween. A fluid infusion fitting 336 is attached to the outer catheter 332 by an adhesive or thermal bonding, as known in the art, at a distance about 70 to 150 cm away from the distal end face 35 of the cylinder 34, preferably at a distance about 80 to 120 cm therefrom. An opening 338 in the outer catheter 332 is in fluid flow communication with the fluid infusion fitting 336 to enable a fluid, such as saline, to be infused through a passageway 339 in the fitting 336 through the passageway 340, and then through the distal end of the catheter 332 to cool the pocket 38 and the cylinder 34 disposed therewithin.

FIG. 4 illustrates yet another embodiment 400 in which the fiber optic cable comprises a bundle of optical fibers 41 wherein the distal ends 46 thereof extend and snugly fit within a recess or cavity 442 defined and extending inwardly into the proximal end face 49 of the cylinder 44 so that the body of the cylinder 44 surrounds the distal ends of the fibers 41. This configuration reduces the scattering of light and the reduction of heat at the juncture or interface between the distal ends 46 of the optical fibers 41 and the proximal end face 49 of the cylinder 44.

In this embodiment, the cylinder 44 additionally includes a recess 445 extending around the peripheral exterior surface thereof and the pocket 48 terminates in an inwardly extending peripheral rib 450. When the sheath 47 is heat shrunk over the optical fibers 41 and the cylinder 44, the rib 450 matingly engages and closes into the circumferential recess 445 in the cylinder 44 to provide a secure fit between the sheath 47 and the cylinder 44. Moreover, in this embodiment, the cylinder 44 includes a proximal portion 44(a) surrounded by the pocket 48 and a distal portion 44(b) which extends beyond the end of the pocket 48 and terminates an atraumatic bulbous or oval shaped tip 45 which has been sandblasted and/or carbon coated as described above.

Figure 5:
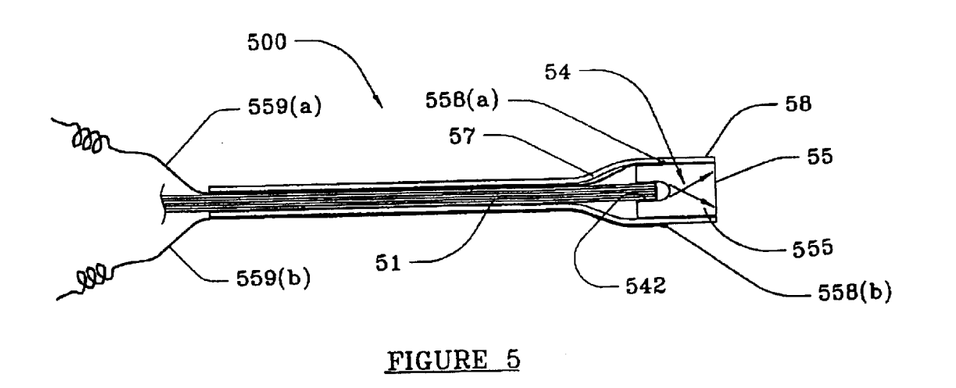
FIG. 5 is an enlarged, broken vertical cross-sectional view of another embodiment of the laser devices of the present invention in which the fiber optic lens includes a concave recess defined therein acting as a convergent lens.

Yet another device embodiment 500 is shown in FIG. 5 in which the distal end portions of the bundle of optical fibers 51 are disposed within a recess or cavity 542 defined and extending inwardly into the proximal end of the cylinder 54 so that the cylinder 54 surrounds the distal end of the fibers 51. Outer face 55 of cylinder 54 is flush with the distal end of pocket 58. In this embodiment, the recess 542 is generally concavely shaped and acts as a convergent lens which allows light energy to travel outwardly from the recess 542 in the direction of arrows 555 at an angle of about 45 degrees relative to the longitudinal axis of the fiber 51.

Optionally, in this particular device embodiment 500, at least one ultrasound emitter 558(a) is attached by an adhesive or the like to the exterior of the cylinder 54 between the cylinder 54 and the sheath 57. The emitter 558(a) extends over about half the length of the pocket 58 and is adapted to create an ultrasound image of the artery surrounding the distal end portion of the device 500. An elongate ultrasound wire 559(a) extends unitarily rearwardly from the ultrasound emitter 558(a) between the fibers 51 and the sheath 57 and then out through the proximal end of the pocket 57 into a source of ultrasound energy and/or a computer system (not shown) for creating an image of the artery.

Alternatively, and as also shown in FIG. 5, an ultrasound emitter 558(b) may be attached by an adhesive or the like to the exterior of the pocket 58 and extends over about half the length of the pocket 58. The wire 559(b) may be attached by an adhesive or the like to the exterior of sheath 57 and extends unitarily rearwardly from the emitter 558(b) to a source of ultrasound energy and/or a computer system (not shown) for the same purpose as discussed above with respect to the emitter embodiment 558(a).

Figure 6:
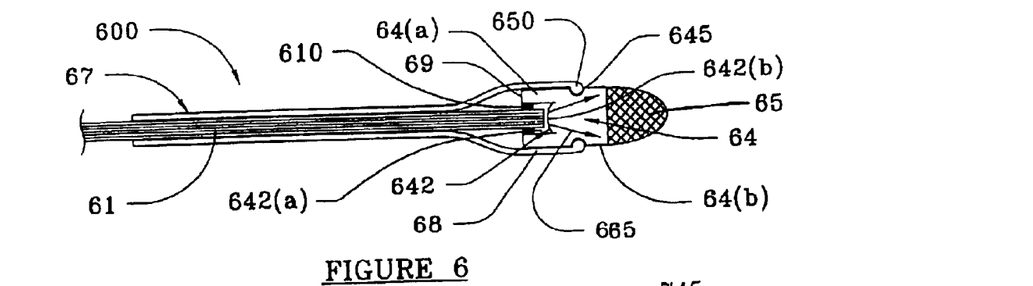
FIG. 6 is an enlarged, broken vertical cross-sectional view of an alternate embodiment of the laser device of the present invention in which the fiber optic lens includes a convex shaped recess defined therein acting as a divergent lens.

FIG. 6 illustrates a further device embodiment 600 in which a recess or cavity 642 is defined and extends into the proximal end face 69 of the cylinder 64. The recess 642 is defined by a sidewall face 642(a) of peripheral side wall of the cylinder 64 and a bottom face surface 642(b) extending therebetween and being convexly shaped as viewed from the proximal end face 69 of the cylinder 64 so that the cylinder 64 acts as a divergent lens with the path of light energy shown by arrows 665 at about a 20 degree angle in the direction, and towards the peripheral outer surface of, the distal end face 65 of the cylinder 64.

A gasket 610 is attached by an adhesive to the outer surface of and surrounds optical fiber 61 and centers optical fiber 61 within recess 642(a) in cylinder 64. Gasket 610 is positioned flush with the proximal end face 69 of the cylinder 64 and abuts and is sealed against the inner cylindrical surface defining the cylinder 64. The distal end portion 64(b) of cylinder 64 is larger in diameter than the proximal end portion 64(a) of cylinder 64, enabling the device 600 to form a channel in the artery or the like at least equal in diameter to the diameter of the hollow sheath 67.

As in the FIG. 4 device embodiment, the pocket 68 terminates in a distal peripheral rib 650 and a circumferential recess 645 is defined in the outer side surface of the cylinder 64. As described above with respect to the FIG. 4, the peripheral rib 650, when heat is applied, is adapted to close into the recess 645 to provide a secure fit between the cylinder 64 and the sheath 67. Also, the proximal portion 64(a) of the cylinder 64 is surrounded by the pocket 68 while the distal portion 64(b) of the cylinder 64 extends outwardly beyond the end of the pocket 68 and terminates in the distal end face or tip 65 which has been sandblasted and/or coated with a layer of carbon. The tip or face 65 can be bulbous or oval shaped, as desired.

Figure 7:
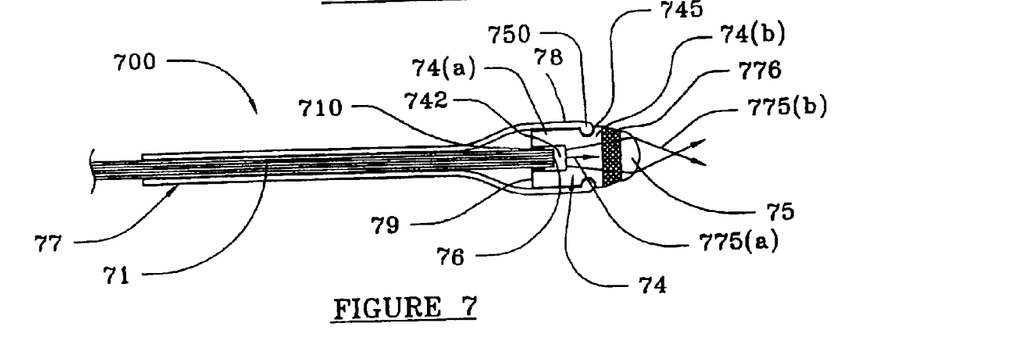
FIG. 7 is an enlarged, broken vertical cross-sectional view of another alternate embodiment of the laser device of the present invention in which the distal end of the fiber optic lens includes a sandblasted and/or carbon coated portion and a clear distal lens portion.

FIG. 7 depicts a yet further device embodiment 700 wherein the cylinder 74 defines a recess or cavity 742 extending into the proximal end face 79 thereof, similar in shape to the recess 442 formed in the cylinder 44 of the device embodiment 400 shown in FIG. 4. The distal ends 76 of the bundle of optical fibers 71 extend into the recess 742, and gasket 710 attached by an adhesive to fiber bundle 71 centers fiber bundle 71 within recess 742 in the same manner as gasket 710. Moreover, the cylinder 74 and the hollow sheath 77 include a circumferential recess 745 and a peripheral rib 750 respectively similar in size and function to the corresponding recess 445 and the rib 450 of the embodiment shown in FIG. 4. Moreover, as in the device of FIG. 4, the proximal portion 74(a) of the cylinder 74 is surrounded by the pocket 78 and the distal end portion 74(b) thereof extends outwardly beyond the end of pocket 78.

The cylinder 74, however, differs in shape from the cylinder 44 of the device 400 in that the distal end portion 74(b) of the cylinder 74 terminates in a clear, ball-shaped distal tip or face 75 and includes a sandblasted and/or carbon coated band portion 776 located aft, and diverging outwardly from, the tip 75. In this configuration, a first portion of the light energy travels longitudinally outwardly from the base of the recess 742 through the cylinder 74 in the direction of arrow 775(a) into the band portion 776 where the light energy is absorbed and converted into thermal energy. Other portions of the light energy travel angularly outwardly from the base of the cylinder recess 742 in the direction of arrows 775(b) into contact with the inner face of the clear, ball-shaped tip 75 which acts as a lens which causes the beams of light energy to converge in a focal energy point located fore of the tip 75.

Figure 8:
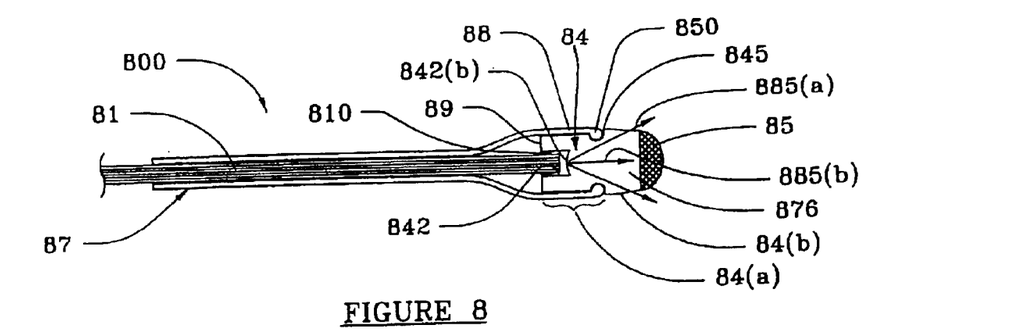
FIG. 8 is an enlarged, broken vertical cross-sectional view of yet another embodiment of the laser device of the present invention.

FIG. 8 depicts yet another device embodiment 800 where the cylinder 84 defines an inner recess 842 extending into the proximal face 89 thereof and a convex lens surface 842(b) similar in size and shape to the recess 642 and the convex lens 642(b) respectively defined in the cylinder 64 of the device 600 disclosed in FIG. 6. Moreover, as shown in FIG. 6, the cylinder 84 also includes an outer circumferential recess 845 defined in the sidewall thereof and an inwardly extending peripheral rib 850 at the tip of the pocket 88 which, when heated, closes into the recess 845 when the cannula 87 is heat shrunk to the cylinder 84. Gasket 810 affixed to fiber bundle 81 centers fiber bundle 81 within recess 842 in the same manner as gaskets 610 and 710.

Moreover, as in FIG. 6, the pocket 88 surrounds only a proximal portion 84(a) of the cylinder 84. The device 800, however, differs in structure from the device 600 in that the cylinder proximal portion 84(a) has a diameter which is less than the diameter of the cylinder distal portion 84(b) to allow the outer circumferential surface of the pocket 88 to be positioned generally flush with the outer circumferential surface of the cylinder distal end portion 84(b).

The distal end portion 84(b) of the cylinder 84 also includes a sandblasted and/or carbon coated rounded end face or tip 85 and a clear band portion 876 diverging outwardly and rearwardly from the tip portion 87 and terminating in the cylinder recess 845.

In device 800 (FIG. 8), light energy travels angularly outwardly in the direction of arrows 885(a) through the cylinder 84 and then out through the cylinder circumferential clear portion 876 to allow, for example, the activation of a photo-active drug which was earlier absorbed by the plaque to be ablated. The remainder of the light energy travels longitudinally outwardly in the direction of arrow 885(b) through the cylinder 84 and into the coated tip portion 85 where the light energy is absorbed to create heat which allows the vaporization of the plaque tissue coming into contact therewith as the device 800 is extended through the blood vessel.

Figure 9A:
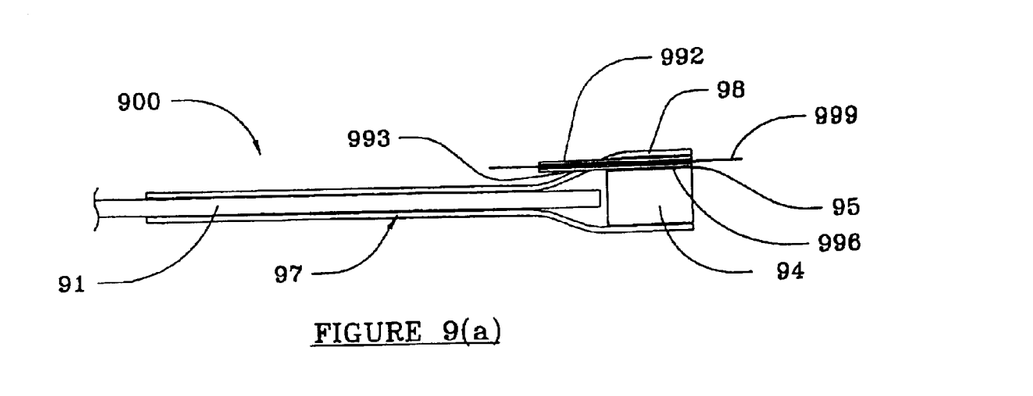
FIG. 9(a) is an enlarged, broken vertical, cross-sectional view of the laser device of FIG. 1(a), in which a tube extends through the distal end of the hollow sheath and through the fiber optic lens, and creates a passageway for a guidewire.
Figure 9B:
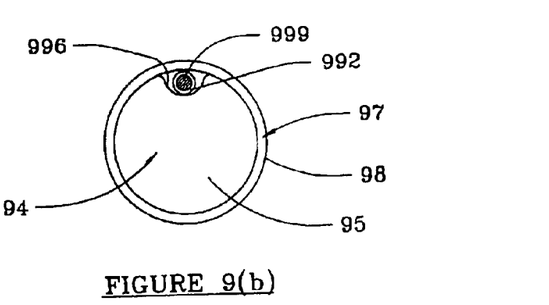
FIG. 9(b) is a vertical end view of the laser device of FIG. 9(a)

The device 900 depicted in FIGS. 9(a) and (b) is similar in structure to the device 10 depicted in FIG. 1(a) except that the cylinder 94 of the device 900 includes a longitudinally extending trough or furrow 996 defined in the cylinder top surface and extending between the opposite end faces of the cylinder 94. The trough 996 is adapted to receive and seat an elongate tube 992 having one distal end face thereof positioned generally flush and co-planar with the distal end face 95 of the cylinder 94 and a proximal end portion extending rearwardly through the pocket 98 and then through an aperture 993 defined in the top wall portion of the pocket 98. The tube 992 sits in the trough 996 in a relationship wherein the inner surface of the pocket 98 surrounding the cylinder 94 is in abutting relationship with the top surface of the tube 992 and the bottom surface of the tube 992 is in abutting relationship with the bottom surface of the trough 996. Alternatively, and although not shown, an obturator rod can be disposed within the recess 996 defined in the cylinder 94, prior to heat shrinking of the hollow sheath 97, so as to maintain a space for later insertion of the tube 992 which can be fixed in place with an adhesive or the like. As in the earlier embodiments, the distal end of fiber optic 91 is spaced from the cylinder 94.

The tube 992 creates a passageway for a guidewire 999 as described in U.S. Pat. Nos. 4,662,368 and 4,773,413, thus enabling the device 900 to be inserted into the blood vessel over the guidewire 999 after the guidewire 999 has first been guided through the blood vessel into position at the site of a target plaque deposit. Rotational torque may be manually applied to the sheath 97 outside of the body, for example at 90 degree intervals, which causes the cylinder 94 to rotate about the guidewire 999 adjacent the target plaque deposit at corresponding 90 degree intervals to allow the device 900 to form a channel through the plaque in the vessel which will be larger than the diameter of the cylinder 94.

The tube 992 can be made of metal, such as hypotubing, a heat resistant plastic, such as PEEK (polyethereketone), Teflon® or a polyamide, which will withstand temperatures of about 335° C., 260° C. or 220° C., respectively, or a heat resistant ceramic, such as a glass-mica ceramic.

Figure 10A:
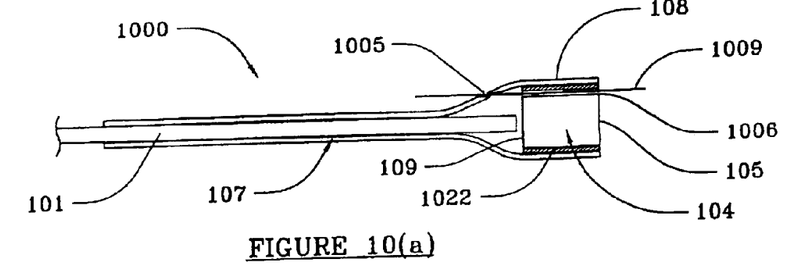
FIG. 10(a) is an enlarged, broken vertical cross-sectional view of an alternate embodiment of the laser device of FIGS. 9(a) and (b)
Figure 10B:
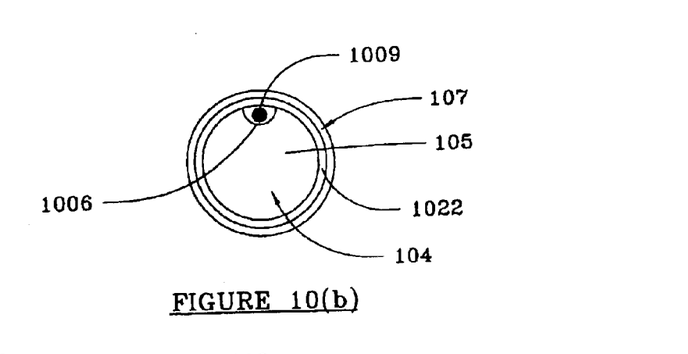
FIG. 10(b) is a vertical end view of the laser device of FIG. 10(a)

In FIGS. 10(a) and (b), the device embodiment 1000 includes a cylinder 104 defining a longitudinally extending trough or furrow 1006 in the top surface thereof and extending between the distal and proximal end faces 105 and 109 respectively. However, instead of a tube 92 as in the device embodiment 900 of FIG. 10(a), the device 1000 includes a ceramic sleeve 1022 which surrounds the cylinder 104. The pocket 108 formed at the end of the sheath 107 is heat shrunk over the fiber 101 and the ceramic sleeve 1022. In accordance with this embodiment, the space created by the longitudinal trough 1006 and the ceramic sleeve 1022 defines an elongate channel for the guidewire 1009. An aperture 1005 defined in the top wall portion of the pocket 108 and located opposite and co-linearly with the proximal end of the trough 1009 completes a passageway which allows the device 1000 to be threaded through the guidewire 1009. The device embodiment 1000 is otherwise similar in structure and function to the device embodiment 900 shown in FIGS. 9(a) and (b).

Figure 11A:
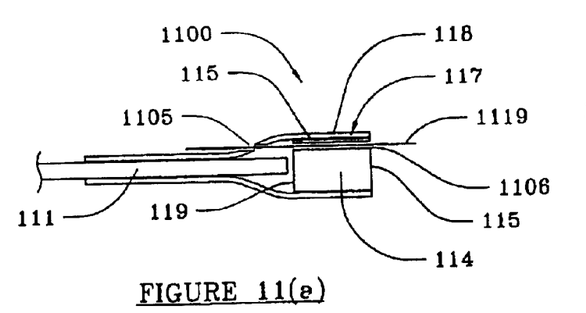
FIG. 11(a) is an enlarged, broken vertical cross-sectional view of another embodiment of the laser device of FIGS. 9(a) and (b)
Figure 11B:
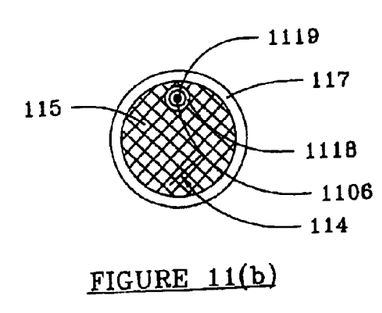
FIG. 11(b) is a vertical end view of the laser device of FIG. 11(a)

The alternate device embodiment 1100 depicted in FIGS. 11(a) and (b) is similar in structure and function to the device embodiments 900 and 1000 respectively in that a fiber optic 111 extends through a sheath 117 and a cylinder 114 is spaced therefrom and seated within a distal sheath pocket 118 except that instead of using a tube or a trough to create a channel for the guidewire 1119, the cylinder 114 defines a bore 1106 extending longitudinally through the body of the cylinder 114 between the distal and proximal end faces 115 and 119 respectively. The guidewire 1119 extends through the bore 1106 and then through a co-linear aperture 1105 which is formed and defined in the top wall of the pocket 118.

FIG. 11(b) illustrates the distal end of the device of FIG. 11(a) wherein all but a small circular area 1118 of the distal end face 115 surrounding the bore 1106 has been sandblasted and/or carbon coated to reduce the risk that the guidewire 1119 will be damaged by thermal energy created in the sandblasted and/or carbon coated distal end face 115 of the cylinder 114 by the emission of laser energy thereinto.

Figure 12A:
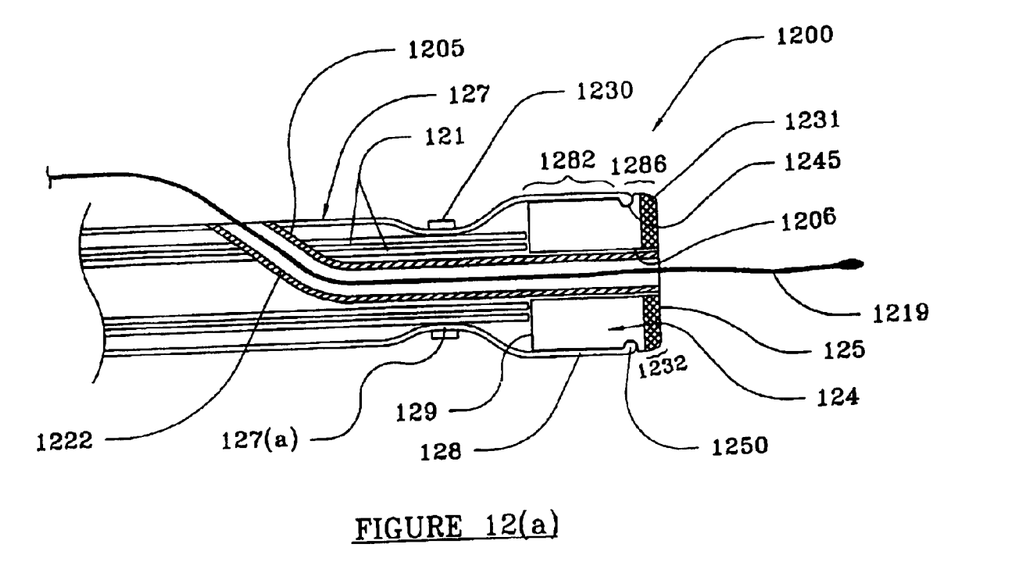
FIG. 12(a) is an enlarged, vertical cross-sectional view of yet another embodiment of the laser device of FIGS. 9(a) and (b)
Figure 12B:
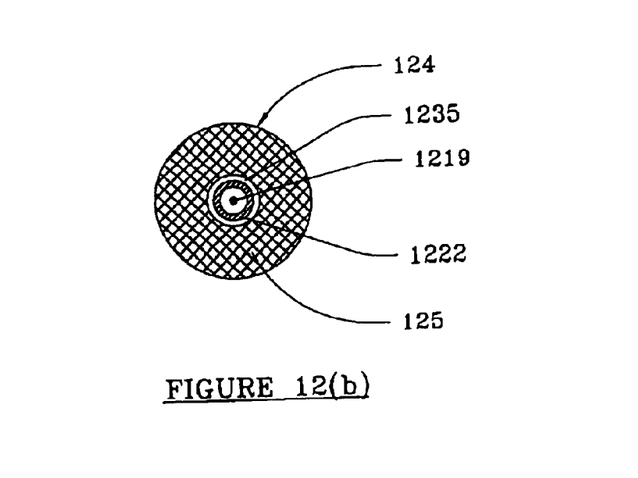
FIG. 12(b) is a vertical end view of the laser device of FIG. 12(a).

FIGS. 12(a) and 12(b) illustrate yet a further alternate device embodiment 1200 in which a guidewire 1219 extends through a tube 1222 which extends through a central longitudinal bore 1206 defined in the body of the cylinder 124 and extending between the respective distal and proximal end faces 125 and 129 thereof. The tube 1222 also extends longitudinally through a portion of the sheath 127 between upper and lower rows of optical fibers 121 and then angularly upwardly and outwardly through an aperture 1205 defined in the top wall of the sheath 127. Alternatively, and although not shown, it is understood that the tube 1222 can exit the sheath 127 at any other point, for example, through the proximal end of the sheath 127.

In this embodiment, the diameter of a proximal portion 1282 of the cylinder 124 is less than the diameter of a distal end portion 1286 of the cylinder 124 such that when the sheath forming pocket 128 is heat shrunk over the cylinder proximal portion 1282, the outer surface of the pocket 128 is generally flush with the outer surface of the cylinder distal end portion 1286 to provide a device having a smooth, atraumatic exterior surface.

As in earlier device embodiments, an inner peripheral rib 1250 formed at the distal end of the pocket 128 is adapted, when heated, to fittingly engage within a cylindrical recess 1245 extending around the periphery of the cylinder 124 to reduce the risk that the cylinder 124 will be dislodged from the pocket 128. Also, in this embodiment, only a segment or band 127(a) of the sheath 127 has been heat shrunk to the optical fibers 121. The segment 127(a) is located aft and spaced from the pocket 128 and the proximal face 129 of the cylinder 124. Moreover, a ring 1230 tightly and fixedly surrounds the heat shrunk segment 127(a) to insure that the sheath 127 does not become dislodged from the bundle of optical fibers 121. Ring 1230 may have a gold plating or coating to make it visible during x-ray viewing.

Moreover, in this particular embodiment the distal circumferential edge 1231 of the distal end face 125 of the cylinder 124 has been rounded into an atraumatic shape. The distal end face 125 of the cylinder 124 can be flat as shown or made into a bullet or cone shape as in some of the other described and depicted device embodiments. In this embodiment, the distal end face 125 and a unitary band 1232 of the cannula distal end portion 1286 have been sandblasted and/or carbon coated so as to absorb the laser energy emitted through the fibers 121.

As shown in FIG. 12(b), a relatively small circular area 1235 of the distal end face 125 of the cylinder 124 immediately surrounding the distal end of the tube 1219 is clear, i.e., has no been sandblasted and/or carbon coated, to minimize heath buildup around the guidewire and thus reduce the risk of damage to the guidewire 1119 by thermal energy.

As can be seen from the above specification and the drawings, what has been described are several different embodiments of a simple, inexpensive, highly reliable, and non-metallic laser angioplasty and channeling device, which radiates substantial heat forwardly, but radiates little or no heat laterally.

Numerous variations and modifications of the several embodiments described above may be effected without departing from the spirit and scope of the novel features of the invention. It is to be understood that no limitation with respect to the specific embodiments illustrated herein is intended or should be inferred. It is, of course, intended to cover by the appended claims all such modifications as fall within the scope of the claims.

We claim:

1. A laser device for forming a channel through an occlusion in a blood vessel, the device comprising:
   a fiber optic conduit adapted for conduit to a source of laser energy; and
   a hollow sheath about distal end portion of the fiber optic conduit and defining a pocket; a fiber optic lens in the pocket and adapted to receive and direct the laser energy emitted from the fiber optic conduit to the occlusion;
   wherein an exterior surface of the lens is sandblasted.
2. The laser device of claim 1 wherein the lens is cylindrical.
3. The laser device of claim 1 wherein the lens extends outwardly beyond the sheath and includes a cylindrical body terminating in a distal spherical end face.
4. The laser device of claim 3 wherein the distal spherical face absorbs a portion of laser energy emitted from the fiber optic conduit through the lens.
5. The laser device of claim 1 wherein the lens extends outwardly beyond the sheath and includes a cylindrical body and a distal oval end face.
6. The laser device of claim wherein the lens extends beyond the sheath and terminates in a distal end face, a portion of the lens between the end face and the sheath being adapted to absorb a portion of laser energy emitted by the fiber optic conduit.
7. The laser device of claim 1 wherein the lens includes an exterior peripheral surface and a peripheral band of the exterior surface absorbs laser energy.
8. The laser device of claim 1 wherein the lens defines a recess adapted to receive the distal end of the fiber optic conduit.
9. The laser device of claim 8 wherein the recess is defined by a peripheral side wall and a concave base.
10. The laser device of claim 8 wherein the recess is rounded.
11. The laser device of claim 1 wherein the lens includes an exterior surface having a peripheral recess defined therein and the sheath includes a distal peripheral rib adapted for engagement in the recess.
12. The laser device of claim 1 wherein the lens includes proximal and distal end portions and the thickness of the proximal end portion is less than the thickness of the distal end portion.
13. The laser device of claim 1 wherein a sleeve surrounds the lens and the sheath surrounds the sleeve.
14. A laser device for forming a channel through an occlusion in a blood vessel, the device comprising:
   a fiber optic conduit adapted for coupling to a source of laser energy; and
   a hollow sheath about distal end portion of the fiber optic conduit and defining a pocket; a fiber optic lens in the pocket and adapted to receive and direct the laser energy emitted from the fiber optic conduit to the occlusion;
   wherein an exterior surface of the lens is carbon coated.
15. A laser device for forming a channel through an occlusion in a blood vessel, the device comprising:
   a fiber optic conduit adapted for coupling to a source of laser energy; and
   a hollow sheath about distal end portion of the fiber optic conduit and defining a pocket; a fiber optic lens in the pocket and adapted to receive and direct the laser energy emitted from the fiber optic conduit to the occlusion;
   wherein the lens defines a recess adapted to receive the distal end of the fiber optic conduit, and
   wherein the recess is defined by a peripheral side wall and a convex base.
16. A laser device for forming a channel through an occlusion in a blood vessel, the device comprising:
   a fiber optic conduit adapted for coupling to a source of laser energy; and
   a hollow sheath about distal end portion of the fiber antic conduit and defining a pocket; a fiber optic lens in the pocket and adapted to receive and direct the laser energy emitted from the fiber optic conduit to the occlusion;

wherein the sheath includes an exterior wall and an aperture defined therein and an elongate wire is adapted to extend through the pocket defined in the sheath and the aperture for guiding the device through the blood vessel.

17. A laser device for forming a channel through an occlusion in a blood vessel, the device comprising:

a fiber optic conduit adapted for coupling to a source of laser energy; and a hollow sheath about distal end portion of the fiber optic conduit and defining a pocket; a fiber optic lens in the pocket and adapted to receive and direct the laser energy emitted from the fiber optic conduit to the occlusion;

wherein the sheath includes an exterior wall and an aperture defined therein, the device further comprising a tube extending through the pocket defined in the sheath and the aperture and an elongate wire extends through the tube and the aperture for guiding the device through the blood vessel.

18. The laser device of claim 17 wherein the lens includes a body having an elongate recess defined in the top thereof, the tube being received in the recess.

19. A laser device comprising a fiber optic conduit adapted for coupling to a source of laser energy and a hollow sheath surrounding a distal end of the conduit and defining a pocket; and a lens mounted in the pocket for directing the laser energy emitted through the conduit; the lens defining a proximal cavity and the distal end of the conduit extending into the cavity;

wherein cavity in the lens is defined by a sidewall and a convex bottom.

20. The laser device of claim 19 wherein the lens includes a proximal cylindrical portion surrounded by the sheath and a distal rounded portion extending outwardly beyond the end of the sheath and composed of a heat absorbing material.

21. The laser device of claim 19 wherein the lens includes a proximal cylindrical portion surrounded by the sheath and a distal oval end portion extending outwardly beyond the end of the sheath and composed of a heat absorbing material.

22. The laser device of claim 21 wherein the distal oval end portion of the lens terminates in a tip and a portion of the lens aft of the tip is composed of a heat absorbing material.

23. The laser device of claim 19 wherein the lens includes a proximal portion surrounded by the sheath and a distal portion extending beyond the end of the sheath.

24. The laser device of claim 23 wherein part of the distal portion is composed of a heat absorbing material.

25. A laser device comprising a fiber optic conduit adapted for coupling to a source of laser energy and a hollow sheath surrounding a distal end of the conduit and defining a pocket; and a lens mounted in the pocket for directing the laser energy emitted through the conduit; the lens defining a proximal cavity and the distal end of the conduit extending into the cavity;

wherein the lens includes an exterior surface having a circumferential recess defined therein and the sheath includes a distal end having an inner peripheral rib, the rib frictionally engaging the recess in the lens.

26. A laser device comprising a fiber optic conduit adapted for coupling to a source of laser energy and a hollow sheath surrounding a distal end of the conduit and defining a pocket; and a lens mounted in the pocket for directing the laser energy emitted through the conduit; the lens defining a proximal cavity and the distal end of the conduit extending into the cavity;

wherein the lens includes a proximal end portion surrounded by the sheath and a distal end portion extending outwardly beyond the end of the sheath, the proximal end portion having a thickness whereby the sheath is flush with the distal end portion of the lens.

27. A laser device comprising a fiber optic conduit adapted for coupling to a source of laser energy and a hollow sheath surrounding a distal end of the conduit and defining a pocket; and a lens mounted in the pocket for directing the laser energy emitted through the conduit; the lens defining a proximal cavity and the distal end of the conduit extending into the cavity;

wherein the sheath includes an exterior wall and an aperture defined therein for receiving an elongate wire.

28. A laser device comprising a fiber optic conduit adapted for coupling to a source of laser energy and a hollow sheath surrounding a distal end of the conduit and defining a pocket; and a lens mounted in the pocket for directing the laser energy emitted through the conduit; the lens defining a proximal cavity and the distal end of the conduit extending into the cavity;

wherein the sheath includes an exterior wall and an aperture defined therein, the device further comprising a tube extending through the pocket defined in the sheath and the aperture, and wherein an elongate wire extends through the tube and the aperture for guiding the device.

29. The laser device of claim 28 wherein the lens defines an elongate trough and the tube is received in the through.

30. A laser device comprising:

a source of laser energy;

a fiber optic conduit adapted for coupling to the source of laser energy;

a hollow sheath surrounding a distal end of the conduit and including a peripheral wall defining a distal pocket and an aperture therein in communication with the pocket, the sheath being adapted to slide along a guide wire extending through the pocket and the aperture for guiding the device through a passageway;

a fiber optic lens received in the pocket; and a tube extending through the pocket defined in the sheath and the aperture, the guide wire extending through the tube and the aperture;

wherein the lens includes a body having an elongate groove defined therein and the tube is received in the groove.

31. A laser device comprising:

a source of laser energy;

a fiber optic conduit adapted for coupling to the source of laser energy;

a hollow sheath surrounding a distal end of the conduit and including a peripheral wall defining a distal pocket and an aperture therein in communication with the pocket, the sheath being adapted to slide along a guide wire extending through the pocket and the aperture for guiding the device through a passageway;

a fiber optic lens received in the pocket; and a tube extending through the pocket defined in the sheath and the aperture, the guide wire extending through the tube and the aperture;

wherein the lens includes a body having an elongate groove defined therein and a sleeve surrounds the lens, the guide wire extending through the channel defined by the groove and the sleeve.

32. A laser device comprising:

a source of laser energy;

a fiber optic conduit adapted for coupling to the source of laser energy;

a hollow sheath surrounding a distal end of the conduit and including a peripheral wall defining a distal pocket and an aperture therein in communication with the pocket, the sheath being adapted to slide along a guide wire extending through the pocket and the aperture for guiding the device through a passageway;

a fiber optic lens received in the pocket; and a tube extending through the pocket defined in the sheath and the aperture, the guide wire extending through the tube and the aperture;

wherein the lens defines a channel therethrough, and the wire extends through the channel.

33. A laser device comprising:

a source of laser energy;

a fiber optic conduit adapted for coupling to the source of laser energy;

a hollow sheath surrounding a distal end of the conduit and including a peripheral wall defining a distal pocket and an aperture therein in communication with the pocket, the sheath being adapted to slide along a guide wire extending through the pocket and the aperture for guiding the device through a passageway;

a fiber optic lens received in the pocket; and a tube extending through the pocket defined in the sheath and the aperture, the guide wire extending through the tube and the aperture;

wherein the lens includes a distal end face and defines an aperture in the distal end face of the lens, and wherein all but the region of the distal end face surrounding the aperture is sandblasted.

34. A laser device comprising:

a source of laser energy;

a fiber optic conduit adapted for coupling to the source of laser energy;

a hollow sheath surrounding a distal end of the conduit and including a peripheral wall defining a distal pocket and an aperture therein in communication with the pocket, the sheath being adapted to slide along a guide wire extending through the pocket and the aperture for guiding the device through a passageway;

a fiber optic lens received in the pocket; and a tube extending through the pocket defined in the sheath and the aperture, the guide wire extending through the tube and the aperture;

wherein the lens includes a distal end face and defines an aperture in the distal end face of the lens, and wherein all but the region of the distal end face surrounding the aperture is coated with carbon.

* * * * *

UNITED STATES PATENT AND TRADEMARK OFFICE
CERTIFICATE OF CORRECTION

PATENT NO.   : 6,845,193 B2
DATED        : January 18, 2005
INVENTOR(S)  : Marvin P. Loeb et al.

It is certified that error appears in the above-identified patent and that said Letters Patent is hereby corrected as shown below:

Column 11,
Line 58, "conduit" (second occurrence) should be -- coupling --.

Column 12,
Line 10, after "claim" insert -- 1 --.

Signed and Sealed this

Twelfth Day of July, 2005

JON W. DUDAS
*Director of the United States Patent and Trademark Office*